United States Patent [19]

Juch et al.

[11] Patent Number: 5,401,514
[45] Date of Patent: Mar. 28, 1995

[54] SOLID, FAST-SOLUBLE PHARMACEUTICAL PREPARATION CONTAINING S-(CARBOXYMETHYL)-L-CYSTEINE AND/OR N-ACETYLCYSTEINE

[75] Inventors: Rolf-Dieter Juch, Wangen; Gerd Birrenbach, Kappel; Christian Pflugshaupt, Haegendorf, all of Switzerland

[73] Assignee: Spirig AG, Pharmazeutische Praeparate, Egerkingen, Switzerland

[21] Appl. No.: 101,086

[22] Filed: Aug. 2, 1993

Related U.S. Application Data

[63] Continuation of Ser. No. 780,705, Oct. 18, 1991, abandoned.

[30] Foreign Application Priority Data

Oct. 19, 1990 [CH] Switzerland .................. 03345/90

[51] Int. Cl.⁶ .................. A61K 9/20; A61K 31/195
[52] U.S. Cl. .................. 424/465; 424/440; 424/441; 424/464; 514/781; 514/784
[58] Field of Search .................. 424/464, 465, 440, 441

[56] References Cited

U.S. PATENT DOCUMENTS 4,968,506  11/1990  Appelgren et al. .................. 424/494
4,970,236  11/1990  Ziggiotti et al. .................. 424/440

OTHER PUBLICATIONS

"Acetylcysteine: A Drug with an Interesting Past and a Fascinating Future," Irwin Ziment, Respiration, 50: Suppl. 1, pp. 26–30 (1986).
"Acetylcysteine: A Drug That is Much More Than a Mucokinetic," I. Ziment, Biomed. & Pharmacother., 42:513–520 (1988).
"Acetylcystein," Information Und Beratung, p. 1873, Detusche Apotheker Zeitung, 130 Jargh, Nr. 34, 23.8 (1990).

Primary Examiner—Thurman K. Page
Assistant Examiner—James M. Spear
Attorney, Agent, or Firm—Lorusso & Loud

[57] ABSTRACT

The compact, solid drug preparation, which contains N-acetylcysteine and/or S-(carboxymethyl)-L-cysteine, is suitable, despite small amounts of inactive ingredients, both for swallowing and for sucking or dissolving in water or an aqueous solution. The compactness of the drug preparation is guaranteed by a high proportion of active ingredients—more than 50% of the total weight—and by a suitable choice of a tableting adjuvant.

24 Claims, 1 Drawing Sheet

SOLID, FAST-SOLUBLE PHARMACEUTICAL PREPARATION CONTAINING S-(CARBOXYMETHYL)-L-CYSTEINE AND/OR N-ACETYLCYSTEINE

This is a continuation of application Ser. No. 07/780,705, filed on Oct. 18, 1991, now abandoned.

This invention concerns an orally administered, solid, fast-soluble pharmaceutical preparation containing S-(carboxymethyl)-L-cysteine and/or N-acetylcysteine that can be dissolved in water or an aqueous solution and sucked or swallowed.

S-(carboxymethyl)-L-cysteine (hereafter called carbocysteine) and N-acetylcysteine are known to be very well tolerated, pharmacologically active substances whose main effect is expectorant. Both active ingredients can be used for treating people with respiratory diseases that lead to the formation of viscous secretions, mucoviscidosis, bronchitis, bronchial asthma, sinusitis, pharyngitis and similar diseases of the respiratory tract. Normally, these mucolytic drugs are administered orally; and the solid drug in the form of powders, granulates or effervescent tablets is dissolved in water before use.

Being aliphatic thio compounds, the substances have an unpleasant odor and taste and high acidity (for example, the pKa value of N-acetylcysteine=3.24). In order to gain patient acceptance, the smell and the taste are usually covered up with a large quantity of inactive ingredients, like, for example, sucrose and highly diverse flavorings.

But since it is a requirement of modem drug morphology to reduce or even eliminate caloric, diabetogenic and cariogenic problems that come from sugar, attempts have recently been made to replace sucrose with sugar alcohols.

The European patent application published under number EP 0 339 508 describes a tablet containing N-acetylcysteine that dissolves very quickly in the mouth and is therefore effective only in this area, which contains alkaline hydrogen carbonates as a buffer and mixtures of sorbitol/fructose, sorbitol/lignite or lignite/fructose as a taste-enhancer in a weight ratio of 0.8:1.2 to 1.2:0.8 and flavorings, wherein the carbohydrate:N-acetylcysteine weight ratio is 20:1 to 50:1.

The European patent application published under number EP 0 340 662 describes a solid drug containing N-acetylcysteine in granular form, which contains lignite as a taste-enhancer, bihydratized saccharin sodium, beta carotene and flavorings. The amount of lignite is 1271 mg per unit for 100 mg of N-acetylcysteine and 2166 mg for 600 mg of N-acetylcysteine.

It can be seen from the state of the art that it takes clever flavoring to obtain a drug with an acceptable taste. This is even more true when large quantities of sucrose must be eliminated in formulating the drug.

Since, according to the state of the art, the amount of inactive ingredients for forms of drugs containing carbocysteine and N-acetylcysteine is so large that drugs from 2 to 3 grams must be produced, the drug must most often be dissolved in water, as described above, dissolved in the mouth or chewed before being taken. On the other hand, only substances with small amounts of inactive ingredients are suitable for swallowing because of the small volume required, which would in turn make sucking or drinking the dissolved drugs impossible because of the odor and the taste. This type of administration, which is limited by the type and the amount of inactive ingredient used, has disadvantages for the consumer.

What is more, carbocysteine (melting point 204°-207° C.) and to an even greater extent N-acetylcysteine (melting point 109°-110° C.) can hardly be compressed into tablets without a prior granulating stage, which complicates and lengthens the production process.

The task of this invention is then to make available a drug preparation containing carbocysteine and/or N-acetylcysteine that is suitable for swallowing because of its volume, which is determined by the small amount of inactive ingredients, and for fast dissolving in water and for sucking because of the type and the amount of inactive ingredients used, and also has an acceptable smell and taste and can be compressed directly into tablets.

The task is solved by making carbocysteine and/or N-acetylcysteine at least 50% by weight of the total weight of the drug preparation, and using as inactive ingredients at least one cellulose and/or a cellulose derivative, at least one soluble sugar alcohol, at least one sweetener, at least one flavoring and, if need be, at least one other tableting adjuvant, like, for example, colloidal soluble amounts at least of one lubricant.

Figure 1:
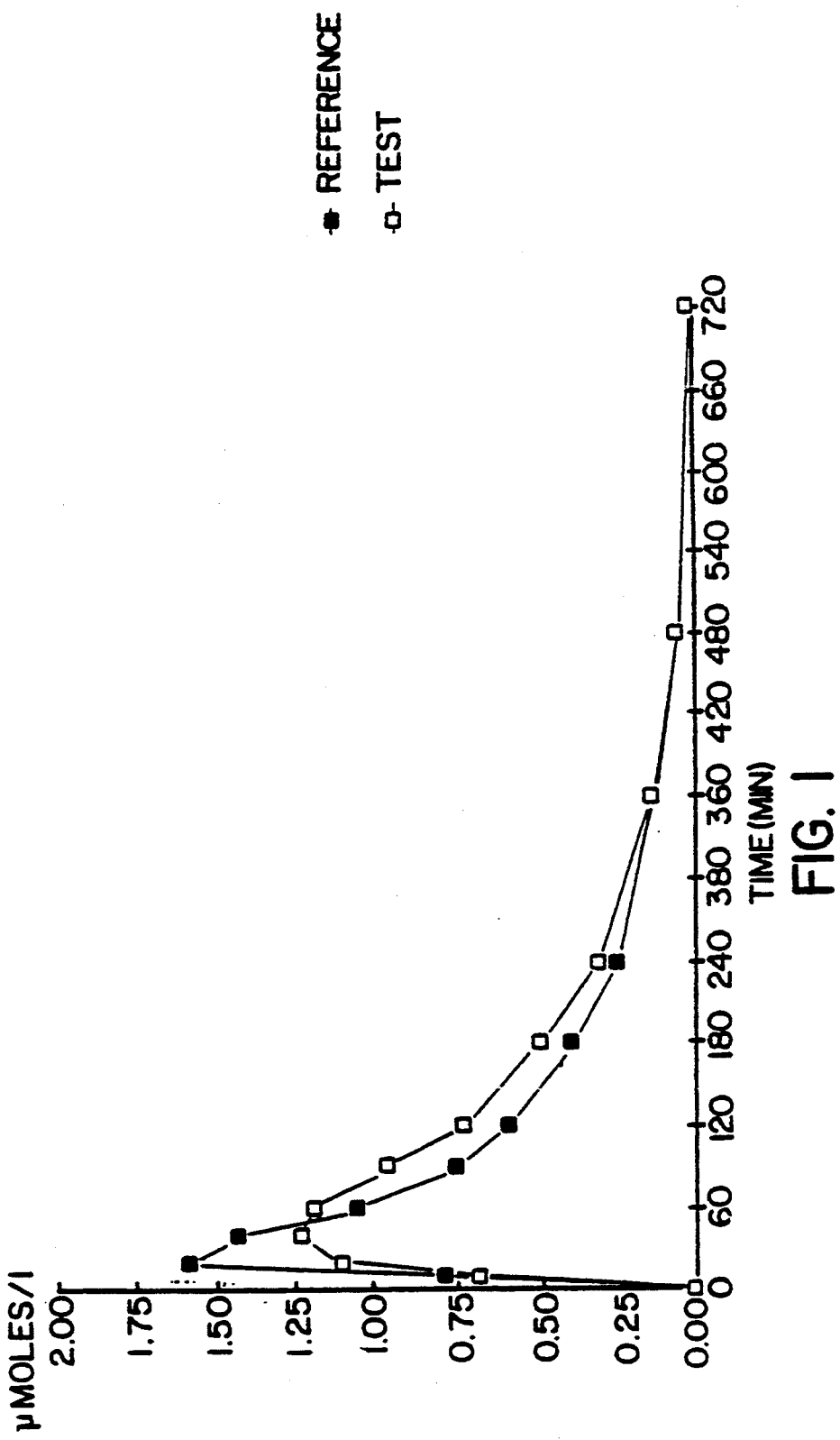
FIG. 1 is a representation of plasma values in a comparative test with a preparation made of a conventional N-acetylcysteine granulate and the drug preparation of the invention.

By choosing suitable inactive ingredients, the components of the mixture can be pressed directly into tablets in the usual way, without having to go through a granulating stage beforehand. This considerably simplifies the production of the tablets in the invention.

A drug preparation of the type previously described in tablet form with less than 50% inactive ingredients by weight, in relation to the total weight of the preparation, is cost-effective.

Despite the small amount of inactive ingredients used, the combination of inactive ingredients surprisingly permits a highly concentrated drug preparation containing carbocysteine and/or N-acetylcysteine with a smell and a taste that are acceptable compared to the state of the art.

Carbocysteine and N-acetylcysteine may be used alone or together in a combination of 1:99 to 99:1 parts.

Microcrystalline cellulose is especially suitable for the cellulose because of its surprisingly good compression properties for carbocysteine and/or N-acetylcysteine, which allow it to be used to compress the mixture directly into tablets. Its proportion to carbocysteine and/or N-acetylcysteine is 0.1% to 25% by weight, preferably 15% to 25% by weight.

For the cellulose derivative, preferably crosslinked sodium carboxymethyl cellulose (NaCMC), which promotes fast solubility of the tablet, and whose amount is 0.1% to 4% by weight, preferably 4% to 12% in relation to the carbocysteine and/or N-acetylcysteine.

For the sugar alcohol, mannitol is especially suitable, as it helps to improve the taste and surprisingly prevents hardening of the tablet during storage. This prevents a delay in the speed with which the tablet dissolves during storage. The mannitol to carbocysteine and/or N-acetylcysteine ratio is 2% to 35% by weight, preferably 25% to 35% by weight.

For the sweetener, mixtures of aspartame and acesulfam-potassium in a ratio of 5:1 to 1:5, preferably 3:1 to 1:1 are suitable. Surprisingly, only 0.1% to 12% by weight sweetener, preferably 4% to 12% by weight in relation to carbocysteine and/or N-acetylcysteine is needed to enhance the taste of the drug preparation decisively.

For the taste, flavoring with lemons, grapefruit and/or pina colada flavors has proven especially suitable. At least one fruit flavor is used in a ratio to carbocysteine and/or N-acetylcysteine of preferably 0.1% to 8% by weight, and 2% to 8% by weight is especially preferred. In this way, the foul-smelling and tasting hydrogen sulfide aroma and taste inherent in the carbocysteine and/or N-acetylcysteine can be covered up in both the tablets dissolved in water and in the tablets to be sucked.

Other suitable inactive ingredients in the tablets are, for example, magnesium stearate and/or colloidal silicic acid, which can be mixed with the tablets for better compressibility. Preferably quantities of 0.1% to 8% by weight, preferably 1% to 4% by weight, in relation to carbocysteine and/or N-acetylcysteine are chosen, so that a colloidal solution of the tablets can still be guaranteed.

The tablets in the invention dissolve clear to colloidal in water or in an aqueous solution in a maximum of 2 minutes, but most often in less than 1 minute. But they can also be swallowed whole or sucked in the mouth, in which case, they disintegrate in a few seconds or in a maximum of one minute, so that carbocysteine and/or N-acetylcysteine can have an effect in the shortest time. And the refreshing, acidic fruity taste helps gives a good feeling, especially if the mucous membranes in the mouth-pharynx area are irritated.

The drug preparations described below are produced in the known way.

EXAMPLE 1

The following powdered components are mixed together homogeneously:

|  | mg per tablet |
| --- | --- |
| N-acetylcysteine | 100 |
| microcrystalline cellulose | 20 |
| mannitol | 30 |
| NaCMC | 7.5 |
| aspartame | 4.5 |
| acesulfam-potassium | 2.0 |
| colloidal silicic acid | 2.0 |
| magnesium stearate | 1.5 |
| lemonade flavoring | 4.0 |
| Total | 171.5 |

The mixture is compressed directly into tablets with a maximum diameter of 7 mm.

The time for the tablet to dissolve in 20° C. water is less than one minute.

EXAMPLE 2

The following powdered components are mixed together homogeneously:

|  | mg per tablet |
| --- | --- |
| N-acetylcysteine | 200 |
| microcrystalline cellulose | 40 |
| mannitol | 60 |
| NaCMC | 15 |
| aspartame | 9 |
| acesulfam-potassium | 4 |
| colloidal silicic acid | 4 |
| magnesium stearate | 3 |
| grapefruit flavoring | 8 |
| Total | 343 |

The mixture is compressed directly into tablets with a maximum diameter of 10 mm.

The time for the tablets to dissolve in 20° C. water is less than one minute.

EXAMPLE 3

|  | mg per tablet |
| --- | --- |
| N-acetylcysteine | 50 |
| S-(carboxymethyl)-L-cysteine | 50 |
| microcrystalline cellulose | 17.5 |
| mannitol | 25.0 |
| NaCMC | 8.0 |
| aspartame | 3.0 |
| acesulfam calcium | 3.0 |
| colloidal silicic acid | 2.0 |
| magnesium stearate | 1.5 |
| lemonade flavoring | 4.0 |
| Total | 164.0 |

The mixture is compressed directly into tablets with a maximum diameter of 7 mm

The time for the tablets to dissolve in 20° C. water is less than one minute.

EXAMPLE 4

|  | mg per tablet |
| --- | --- |
| S-(carboxymethyl)-L-cysteine | 100 |
| microcrystalline cellulose | 20.0 |
| mannitol | 15.0 |
| NaCMC | 5.0 |
| aspartame | 1.4 |
| acesulfam calcium | 5.6 |
| colloidal silicic acid | 1.5 |
| magnesium stearate | 1.0 |
| lemonade flavoring | 5.0 |
| Total | 154.5 |

The mixture is compressed directly into tablets with a maximum diameter of 7 mm.

The time for the tablets to dissolve in 20° C. water is less than one minute.

EXAMPLE 5

A comparative test with a preparation made of a conventional N-acetylcysteine granulate on 10 subjects surprisingly showed than the drug preparation in the invention led no better bioavailability of the active ingredient (higher AUC). A process for quantitative determination of N-acetylcysteine in plasma was used, which split the active ingredient with tributyl phosphine reductively and derivatized in with a post-HPLC column using o-phthalaldehyde.

By this process, endogenous average concentrations of 0.08 $\mu$M were measured for the first time. The active ingredient was still found in the plasma 12 hours after oral application of one 200 mg dose. The $C_{max}$ values were up to 20 times higher than the endogenous plasma values of the test persons (see FIG. 1 and Table 1). The comparative test is documented in Biopharmaceutics & Drug Disposition, Vol. 12, 343-353 (1991).

TABLE 1

Individual and mean (±SD) pharmacokinetic parameters after oral administration of 200 mg of N-acetylcysteine in the Test (T) and Reference (R) formulations

| Subject | $AUC_{INF}$ h.µmoles $l^{-1}$ T | R | T/R | $C_{max}$ µM T | R | T/R | $t_{max}$ h T | R | T-R | $t_{\frac{1}{2}}$ h T | R | MRT h T | R | T/R |
|---|---|---|---|---|---|---|---|---|---|---|---|---|---|---|
| 1 | 4.71 | 4.00 | 1.18 | 1.76 | 1.67 | 1.05 | 0.67 | 0.33 | 0.33 | 2.20 | 1.96 | 3.07 | 2.96 | 1.04 |
| 2 | 1.82 | 1.60 | 1.13 | 0.56 | 0.56 | 1.0 | 1.0 | 1.0 | 0 | 2.74 | 2.70 | 3.68 | 3.59 | 1.03 |
| 3 | 3.19 | 2.63 | 1.21 | 1.10 | 1.37 | 0.80 | 1.0 | 0.67 | 0.33 | 1.91 | 1.93 | 2.82 | 2.58 | 1.09 |
| 4 | 3.55 | 5.41 | 0.66 | 1.71 | 2.44 | 0.70 | 0.33 | 0.67 | −0.33 | 1.36 | 1.89 | 2.47 | 2.61 | 0.95 |
| 5 | 3.43 | 3.47 | 0.99 | 1.19 | 1.39 | 0.86 | 0.33 | 0.33 | 0 | 2.16 | 1.73 | 3.16 | 2.78 | 1.14 |
| 6 | 3.86 | 2.32 | 1.66 | 1.92 | 1.46 | 1.32 | 0.33 | 0.33 | 0 | 1.67 | 0.86 | 2.33 | 1.97 | 1.18 |
| 7 | 4.06 | 2.70 | 1.50 | 1.57 | 1.17 | 1.34 | 0.67 | 0.33 | 0.33 | 0.92 | 1.28 | 2.22 | 2.23 | 1.0 |
| 8 | 3.67 | 3.90 | 0.94 | 0.83 | 1.54 | 0.54 | 2.0 | 0.33 | 1.67 | 1.90 | 2.95 | 3.89 | 3.72 | 1.05 |
| 9 | 2.98 | 2.58 | 1.15 | 1.22 | 1.83 | 0.67 | 0.33 | 0.33 | 0 | 2.16 | 1.61 | 2.72 | 2.11 | 1.29 |
| 10 | 7.23 | 7.04 | 1.03 | 2.70 | 3.27 | 0.83 | 1.0 | 0.67 | 0.33 | 1.93 | 2.24 | 3.05 | 2.59 | 1.18 |
| Mean | 3.85 | 3.57 | | 1.46 | 1.67 | | 0.77 | 0.50 | | 1.90 | 1.92 | 2.94 | 2.71 | |
| SD | 1.41 | 1.62 | | 0.61 | 0.74 | | 0.52 | 0.24 | | 0.50 | 0.62 | 0.55 | 0.58 | |

We claim:

1. An orally administered palatable, fast-soluble, (soluble in a maximum of two minutes), solid drug preparation containing S-(carboxymethyl)-L-cysteine and/or N-acetylcysteine, whose proportion by weight of active ingredient is at least 50% of the total weight of the drug preparation and whose remaining amount contains as inactive ingredients at least one cellulose and/or carboxymethyl cellulose, at least one soluble sugar alcohol, at least one sweetener, at least one flavoring.

2. A drug preparation according to patent claim 1, which contains in relation to S-(carboxymethyl)-L-cysteine and/or N-acetylcysteine, by weight 0.1%–25% cellulose and/or 0.1%–12% carboxymethyl cellulose, 2%–35% sugar alcohol, 0.1%–12% sweetener, 0.1%–8% flavoring.

3. A drug preparation according to patent claim 2, which contains, in relation to S-(carboxymethyl)-L-cysteine and/or N-acetylcysteine, by weight 15%–25% cellulose and/or 4%–12% carboxymethyl cellulose, 25%–35% sugar alcohol, 4%–12% sweetener, 2%–8% flavorings.

4. A drug preparation according to patent claim 1, which contains 50 to 400 mg S-(carboxylmethyl)-L-cysteine and/or N-acetylcysteine in tablet form having a diameter of 5 to 12 mm.

5. A drug preparation according to patent claim 1, characterized by the fact that microcrystalline cellulose is used as the cellulose.

6. A drug preparation according to patent claim 1, characterized by the fact that said carboxymethyl cellulose is sodium carboxymethyl cellulose.

7. A drug preparation according to patent claim 1, characterized by the fact that mannitol is used as a sugar alcohol.

8. A drug preparation according to patent claim 1, characterized by the fact that mixtures of aspartame and acesulfam potassium are used as sweeteners in a ratio of 5:1 to 1:5.

9. A drug preparation according to patent claim 1, characterized by the fact that at least one fruit flavor is used as a flavoring.

10. The drug preparation according to claim 1 further comprising at least one other tableting adjuvant.

11. An orally administered palatable, fast-soluble, (soluble in a maximum of two minutes), solid drug preparation containing S-(carboxymethyl)-L-cysteine and/or N-acetylcysteine, whose proportion by weight of active ingredient is at least 50% of the total weight of the drug preparation and whose remaining amount contains as inactive ingredients at least one cellulose, at least one soluble sugar alcohol, at least one sweetener, at least one flavoring wherein said preparation contains 100 mg of N-acetylcysteine or S-(carboxymethyl)-L-cysteine or mixtures thereof, 20 mg of microcrystalline cellulose, 30 mg of mannitol, 7.5 mg of sodium carboxymethyl cellulose, 4.5 mg of aspartame, 2.0 mg of acesulfam potassium 2.0 mg of colloidal silicic acid, 1.5 mg of magnesium stearate and 4.0 mg of lemonade flavoring.

12. An orally administered palatable, fast-soluble, (soluble in a maximum of two minutes), solid drug preparation containing S-(carboxymethyl)-L-cysteine and/or N-acetylcysteine, whose proportion by weight of active ingredient is at least 50% of the total weight of the drug preparation and whose remaining amount contains as inactive ingredients at least one cellulose, at least one soluble sugar alcohol, at least one sweetener, at least one flavoring;
containing 200 mg of N-acetylcysteine or S-(carboxymethyl)-L-cysteine or mixtures thereof, 40 mg of microcrystalline cellulose, 60 mg of mannitol, 15 mg of sodium carboxymethyl cellulose, 9 mg of aspartame, 4 mg of acesulfam potassium, 4 mg of colloidal silicic acid, 3 mg of magnesium stearate and 8 mg of grapefruit flavoring.

13. A process for producing a drug preparation according to patent claim 1, characterized by the fact that N-acetylcysteine or S-(carboxymethyl)-L-cysteine or mixtures thereof are compressed directly into tablets with the inactive ingredients.

14. A drug preparation that can be swallowed, sucked and dissolved in aqueous solution according to patent claim 1.

15. A drug preparation according to patent claim 1 that disintegrates when sucked or dissolved in water or an aqueous solution within one minute.

16. A process for treating people with respiratory diseases that lead to the formation of viscous secretions, mucoviscidosis, bronchitis, bronchial asthma, sinusitis, pharyngitis by the administration of an effective amount of a drug preparation according to claim 1.

17. A drug preparation according to patent claim 10, characterized by the fact that a colloidal soluble amount of at least one lubricant is used as a tableting adjuvant.

18. The drug preparation according to claim 1 further comprising 0.1%–8% tableting adjuvant.

19. The drug preparation according to claim 3 further comprising 2%–8% tableting adjuvant.

20. The drug preparation according to claim 8 wherein said ratio is 3:1 to 1:1.

21. The drug preparation of claim 9 wherein said fruit flavor is lemonade, grapefruit juice or pina colada flavor.

22. The drug preparation according to claim 17 wherein said lubricant comprises magnesium stearate and/or colloidal silicic acid.

23. The process of treating people in need of an expectorant by the administration of an effective amount of a drug preparation according to claim 1.

24. An orally administered palatable, fast-soluble, (soluble in a maximum of two minutes), solid drug preparation in swallowable tablet form containing S-(carboxymethyl)-L-cysteine and/or N-acetylcysteine, whose proportion by weight of active ingredient is at least 50% of the total weight of the drug preparation and whose remaining amount contains as inactive ingredients at least one cellulose and/or carboxymethyl cellulose, at least one soluble sugar alcohol, at least one sweetener, at least one flavoring.

* * * * *

UNITED STATES PATENT AND TRADEMARK OFFICE
CERTIFICATE OF CORRECTION

PATENT NO. : 5,401,514
DATED : March 28, 1995
INVENTOR(S) : Juch et al.

It is certified that error appears in the above-indentified patent and that said Letters Patent is hereby corrected as shown below:

Column 1, Line 33: Delete "modem" and insert --modern--;

Column 4, Line 54: Delete "than" and insert --that--;

Column 4, Line 55: Delete "no" and insert --to--; and

Column 4, Line 59: Delete "in" and insert --it--.

Signed and Sealed this

Twenty-ninth Day of August, 1995

Attest:

BRUCE LEHMAN

Attesting Officer　　　Commissioner of Patents and Trademarks